United States Patent [19]
Mayer

[11] Patent Number: 6,009,743
[45] Date of Patent: Jan. 4, 2000

[54] APPARATUS AND METHOD FOR ONLINE OR OFFLINE MEASUREMENT OF VAPOR TRANSMISSION THROUGH SHEET MATERIALS

[75] Inventor: William N. Mayer, White Bear Lake, Minn.

[73] Assignee: Mocon, Inc., Minneapolis, Minn.

[21] Appl. No.: 09/138,890

[22] Filed: Aug. 24, 1998

[51] Int. Cl.[7] ............................ G01N 15/08; F26B 25/00
[52] U.S. Cl. ................................................. 73/38; 34/242
[58] Field of Search ....................... 73/38, 865.5; 34/242, 34/209

[56] References Cited

U.S. PATENT DOCUMENTS

| 4,335,610 | 6/1982 | Scott | 73/38 |
| 4,492,041 | 1/1985 | Mansour | 34/15 |

*Primary Examiner*—Hezron Williams
*Assistant Examiner*—Jay L. Politzer
*Attorney, Agent, or Firm*—Paul L. Sjoquist

[57] ABSTRACT

An apparatus for measuring and comparing the permeant transmission rate through film material on a moving conveyor, including a first and second chamber through which the film material is moved, a permeant supply to the first chamber and a permeant detector connected to the second chamber. A computer processor is connected to the detector to quantify the detected amounts of permeant and to compare the detected permeant amounts with similar amounts detected for a different material sample, and for determining the permeant transmission rate characteristics of the film material by such comparison.

15 Claims, 3 Drawing Sheets

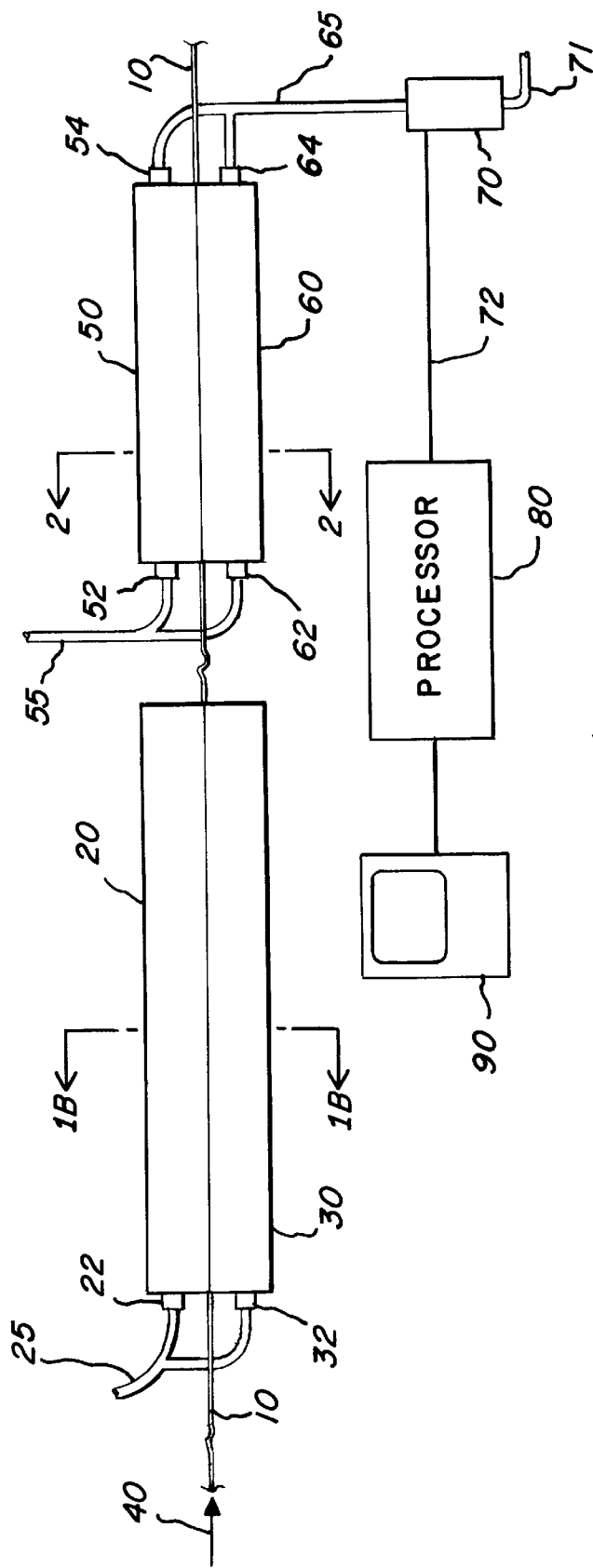
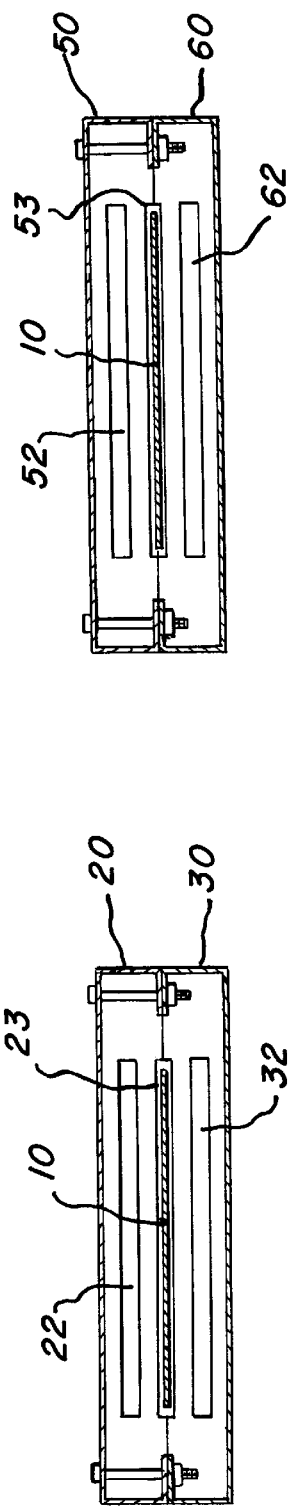

APPARATUS AND METHOD FOR ONLINE OR OFFLINE MEASUREMENT OF VAPOR TRANSMISSION THROUGH SHEET MATERIALS

BACKGROUND OF THE INVENTION

The present invention relates to a vapor detector for measuring vapor transmission rate characteristics of sheet materials; more particularly, the invention relates to determining the vapor transmission characteristics of sheet materials online, during a manufacturing process. The present invention is also useful for measuring vapor transmission characteristics of materials offline, by way of comparing characteristics of two or more different samples of the material, in a very quick procedure.

Certain apparatus for measuring vapor flow rate using particular sensor devices are known in the prior art. One type of sensor device typically provides an electrochemical transformation in response to the presence of the vapors being measured, as for example, measuring oxygen permeating through a membrane. One such detector is disclosed in U.S. Pat. No. 3,223,597, issued Dec. 14, 1965, and another form of oxygen detector is disclosed in U.S. Pat. No. 4,085,024, issued Apr. 18, 1978. These devices utilize a glass envelope which encloses an anode overlaid with nickel-cadmium (Ni—Cd), wrapped with an insulating material, and having a carbon fiber cathode overlying the insulating material. Electrical conductors attached to each of the anode and cathode are brought to the outside of the glass envelope through sealed openings. A gas inlet and gas outlet is provided through the glass envelope, to permit the flow-through passage of an oxygen-carrying gas. The interior of the glass tube is filled or partially filled with potassium hydroxide (KOH). The oxygen molecules in the gas cause an electrochemical reaction to occur between the anode and cathode, whereby a small current is developed through the conductors, and the magnitude of the current is representative of the oxygen content of the gas.

Other types of sensors utilize predetermined wavelengths of radiated energy to detect the presence of certain vapors or gases, as for example, infrared detectors for detecting the presence of water vapor and the like.

It is usually desirable to make measurements with these devices under equilibrium conditions, where a vapor or gas source is confined in a chamber on one side of a membrane, and a vapor or gas detector is connected to a chamber on the other side of the membrane, and conditions are held constant until the vapor or gas permeating through the membrane reaches a constant level, where as much vapor or gas leaves the downstream side of the membrane as enters the upstream side of the membrane. The test for making this measurement necessarily takes a considerable amount of time, as it can take many hours for the conditions to stabilize.

It is also possible to measure the vapor or gas transmission characteristics by a process that measures the outgassing characteristics of the material. In this circumstance, the material is first saturated in the gas or vapor of interest, and then is placed in a closed chamber where the vapor which outgasses from the material can be measured. The rate at which the vapor outgasses provides a measure of the vapor transmission characteristics of the material. An apparatus and method which describes this technique is found in my U.S. Pat. No. 5,591,898, issued Jan. 7, 1997, and entitled "Method for Measuring Material Permeability Characteristics."

It is also possible to measure the vapor or gas transmission characteristics of a material by a process that measures the outgassing characteristics of the material, even if the material has not been totally saturated in the gas or vapor of interest. This process is possible because the outgassing characteristics of any material follow a predictable complex exponential curve over time, and partial saturation of a material causes outgassing to occur along the same curve as complete saturation of the material; collection of only a few data points along this curve enables one to reconstruct the outgassing curve as though the material had been completely saturated.

Each of the foregoing processes provide a technique for obtaining a measure of transmission rate of a particular gas or vapor through a particular material, and therefor provides a quantitative value for the gas or vapor transmission rate of the particular material. This information is valuable in enabling a manufacturer to select, for example, the proper materials for packaging particular foods, liquids, medicines, etc., where contamination of the product within a package, by gases or vapors passing through the package material, may degrade or spoil the product. However, each of the foregoing processes require some time to complete, at least several hours, and therefore can only be practically performed under off-line conditions where the packaging materials may be tested on a statistical sampling basis. It would be extremely desirous if the transmission rate characteristics of a material could be obtained on-line; i.e., while the material is being manufactured or while the product packaging process is being performed. Furthermore, it would be desirous if the measurement of transmission rate characteristics of materials being manufactured could serve as a qualitative standard to regulate the manufacture of the packaging material, or by monitoring the vapor barrier qualities of a packaging material while the product packaging operation proceeds, wherein the manufacturing line could be shut down whenever the vapor barrier qualities of the packaging material on the line deviates outside a predetermined range of desired transmission rate characteristics.

SUMMARY OF THE INVENTION

The present invention comprises a permeant chamber for enclosing about a movable film which is arranged on a manufacturing assembly line, the film being arranged to travel along a linear path of travel. The invention also includes a measurement chamber which is arranged downstream from the permeant chamber, and which is connected to a permeant detector, which is some form of vapor or gas detector. The permeant chamber and the measurement chamber each have a particular length dimension along the linear path of travel of the film, which is a function of the rate of linear film travel and the rate of permeant absorption into the material and the outgassing rate of permeant from the material, as well as a function of the sensitivity of the permeant detecting device. The permeant chamber must be sufficiently long to permit a measurable amount of permeant, usually in the form of a vapor or gas, to become absorbed into the material while the material travels through the permeant chamber. The measurement chamber must be sufficiently long to permit a measurable amount of permeant to outgas from the material while the material travels through the measurement chamber; the detector must be sufficiently sensitive to measure the permeant which is outgassed from the material during its travel through the measurement chamber.

The method of the present invention can also be used to measure vapor or gas transmission rates through materials on an off-line basis, by outgassing the material which may be only partially gas or vapor-saturated, and comparing the outgassing data with a sample previously taken wherein the outgassing curve of the material was developed; the advantage of the method is that it enables transmission rates of gases or vapors through materials to be measured and calculated very much faster than previously known methods. Using the method, the outgassing data is taken at a single point in time, or on a continuous basis, and the data point or cumulative outgassed permeant is compared with the value of the premeasured outgassing curve at the same relative point in time or under the same continuous conditions; the ratio of the two measurements is directly related to the ratio of the transmission rates of the two material samples.

It is a principal object and advantage of the present invention to provide an apparatus capable of measuring the transmission rate of vapors or gases through a film material as the material is being manufactured.

It is another object and advantage of the present invention to measure online vapor or gas transmission rates by measuring partial outgassing from a material during the material manufacturing process, and formulating the vapor or gas transmission rate characteristics of the material by comparison of the measured outgassing with previously measured vapor or gas transmission rates of the same or similar material, made under isostatic conditions.

It is yet another advantage and object of the present invention to provide a method for calculating the transmission rate of a material by comparison of at least one outgassing data point taken from testing the material, and comparing the data point with a comparable data point from a previously tested sample of the same or similar material, taken at the same relative time on its outgassing curve.

Other and further objects and advantages of the invention will become apparent from the following specification and claims and with reference to the appended drawings.

BRIEF DESCRIPTION OF THE DRAWINGS

FIG. 1A shows a diagrammatic representation of one apparatus construction of the present invention;

FIG. 1B shows a view taken along the lines 1B—1B of FIG. 1A;

FIG. 2 shows a view taken along the lines 2—2 of FIG. 1A; and

DESCRIPTION OF THE PREFERRED EMBODIMENT

Figure 3:
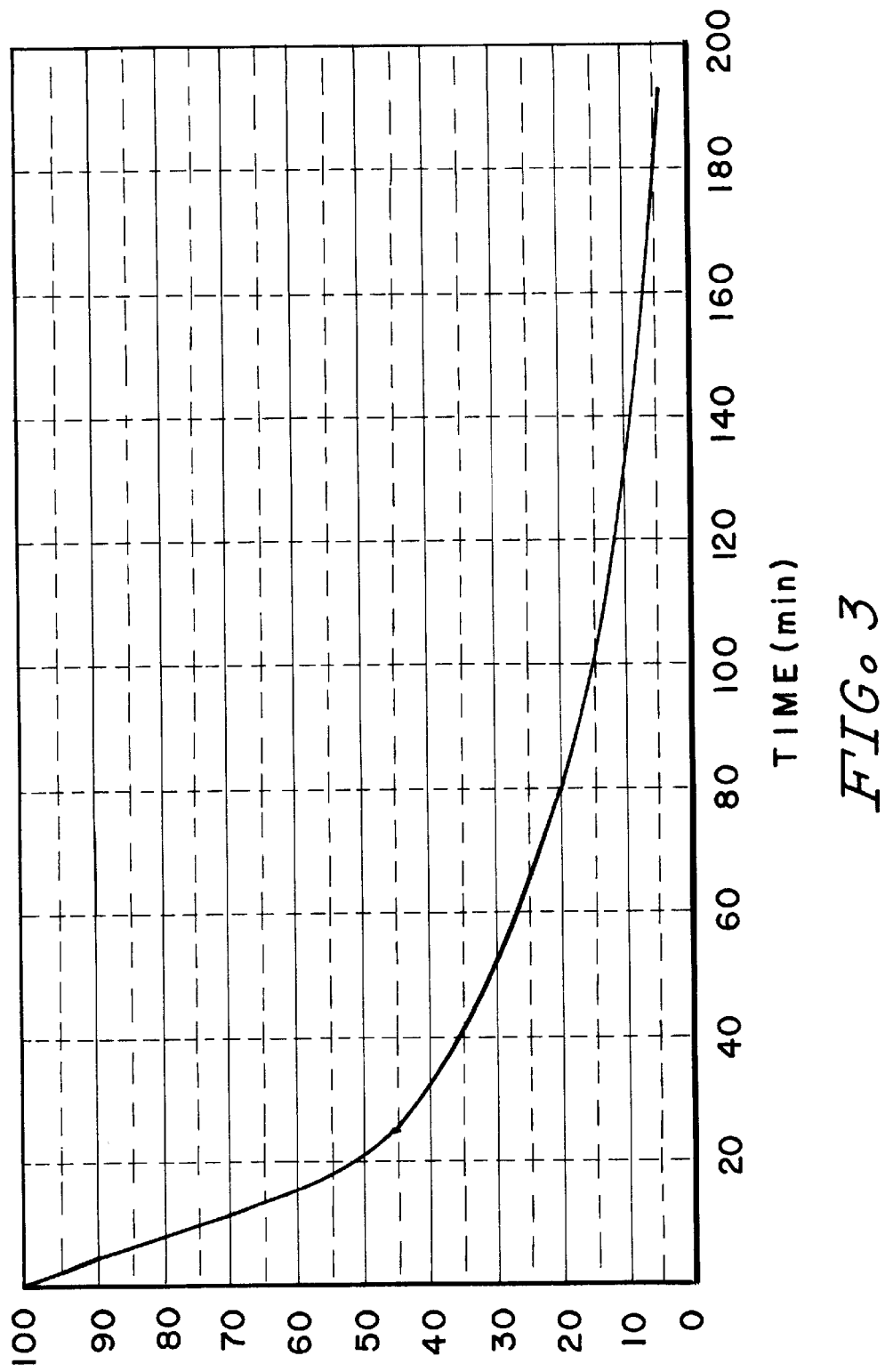
FIG. 3 is a graph showing transmission rate as a function of time for a typical film material, wherein the time scale may be many hours.

A prerequisite to the use of the apparatus of this invention, and using the method described herein, is to develop the curve which quantitatively shows the outgassing characteristics of the base material undergoing testing. This base curve is a complex exponential curve as described in my U.S. Pat. No. 5,591,898, and when the curve becomes quantified the coefficients and exponential constants yield data from which the film permeability, solubility, and diffusion coefficient can be developed, as well as the vapor or gas transmission rate characteristics of the film. A determination of this curve can be made under isostatic conditions as described in the prior art or using the method for measuring film outgassing characteristics as described in the aforementioned U.S. Patent.

Once this curve has been developed for a sample of a given material, subsequent samples of the material will yield the same curve unless the material composition changes. If the material composition changes, a different complex exponential curve will be necessary for determining the film characteristics, and in particular, in determining the vapor or gas transmission rate characteristics for the film having a different material composition, and it follows that each of the data points which make up the different curve will be different from the data points making up the initial or base curve, when compared under some normalized set of conditions such that the data point comparison can be made. For example, if the base sample of film material were initially fully saturated with a gas or vapor, and the outgassing of the film sample were recorded over units of time, the outgassing data points vs. time can be plotted to develop an outgassing curve for the film sample.

Subsequently, if a different sample of the film was also fully saturated with the gas or vapor and the outgassing of this second film sample was recorded over the same units of time, the outgassing curve for the second film sample can be developed, and a comparison of the recorded data points for the second film with the recorded data points for the first film, taken at the same relative increments of time, will yield a value which represents a comparison of the respective film sample transmission rates.

In other words data point X1, taken at time t1 for film sample 1, is to the vapor transmission rate TR1 of film 1, as data point X2, taken at time t1 for the film sample 2, is to the vapor transmission rate TR2 of film 2:

$$X1/TR1 = X2/TR2 \text{ (both at time t1)};$$

or expressing the equation in terms of calculating the (unknown) transmission rate (TR2) of film 2, if the transmission rate (TR1) of film 1 were known:

$$TR2 = X2/X1 \; TR1.$$

The foregoing equation enables a comparison transmission rate characteristics of two film samples by a comparison of only a single data point on the respective outgassing curves of the two film samples.

Of course, a quantitative value of transmission rate for at least one of the samples requires an analysis of accumulated recorded data for the sample sufficient to develop the complete complex exponential curve for the sample, but the foregoing equation shows that this rather complex analysis need be done only one time for one film sample, and the single data point comparison can provide the transmission rate for a subsequent sample by the data point comparison method.

Alternatively, the measurement data can be cumulatively collected over a predetermined time span, provided that the collected samples are obtained under the same conditions for the two material samples which are to be compared.

Referring first to FIG. 1A, the invention is shown in diagrammatic form in conjunction with an assembly line for the manufacture of a film 10. An upper permeant chamber 20 is positioned atop the movable film 10, and a lower permeant chamber 30 is positioned on the underside of the movable film 10, with a film entrance and exit slot arranged at the interface between the upper chamber 20 and the lower chamber 30. A controlled atmosphere is maintained in both the upper chamber 20 and the lower chamber 30 by admitting a vapor having a predetermined relative quantity of permeant vapor through gas inlets 22 and 32, which are connected to a conduit 25 which is itself connected to a source of permeant (not shown). In one embodiment of the invention the permeant can be humidified vapor, and the source of this vapor can be a controlled humidity source.

An upper measurement chamber 50 and a lower measurement chamber 20 are positioned downstream from the permeant chambers 20 and 30. Each of the chambers 50 and 60 has an entrance an exit slot along their respective interface edges to permit the film 10 to enter and leave the chambers 50 and 60. Gas inlets 52 and 62 are respectively formed on the upstream edges of chambers 50 and 60, and the inlets 52 and 62 are connected to a conduit 55 which is connected to an inert gas source (not shown). One inert gas source which is suitable for this purpose is nitrogen. Gas outlets 54 and 64 are connected along the downstream edge of chambers 50 and 60, and these outlets are connected to a conduit 65 which leads to a detector 70. Detector 70 has an outlet 71, and has electrical connections 72 which develop a voltage representative of the permeant content of the vapor flowing through detector 70. The electrical connections 72 are connected to a processor 80, which may be a commercially available computer processor. The electrical signals carried by connections 72 are translated into digital values in processor 80, and are visually displayed on a display device 90, which may be a conventional cathode ray tube display. The signals may also be recorded and stored for future statistical analysis in the processor 80.

FIG. 1B shows a view taken along the lines 1B—1B of FIG. 1A. An interface slot 23 is formed along the entrance edges of chambers 20 and 30, and a similar exit slot is formed along the exit edges of chambers 20 and 30. Inlets 22 and 32 provide for the introduction of a controlled permeant along the entrance edges of chambers 20 an 30. Film 10 is movable through the entrance and exit slots in the direction indicated by arrow 40, and each incremental section of film 10 resides inside the permeant chamber for a length of time determined by dividing the linear length of the permeant chamber by the rate of travel of film 10.

FIG. 2 shows a view taken along the lines 2—2 of FIG. 1A. An interface slot 53 is formed along the entrance edges of chambers 50 and 60, and a similar exit slot is formed along the exit edges of chambers 50 and 60. Gas inlets 52 and 62 provide for the introduction of an inert gas, such as nitrogen, into chambers 50 and 60, and gas outlets 54 and 64 provide for the exit of gas from chambers 50 and 60. The exit gas will consist of inert gas plus a certain amount of permeant which will outgas from the film 10 while the film 10 is passing through the chambers 50 and 60. This composite gas is passed into a detector 70 via conduit 65, where the permeant content of the composite gas causes an electrical signal to be developed which is representative of the amount of permeant which outgassed from film 10. The electrical signal is passed to processor 80 for further processing, including determining the permeant transmission rate of the material which makes up film 10, and measuring the variation in permeant transmission rate of the material over the manufacturing cycle.

FIG. 3 shows a graph illustrating the outgassing curve for a typical, representative material such as Mylar® plastic sheet material of about 5-mil thickness. The vertical scale of the graph is shown in arbitrary dimensional units 0–100, which reflect the instantaneous desorption rate; i.e., outgassing rate, usually measured in cubic centimeters per square meter per day ($cc/M^2/day$), which quantifies the number of cubic centimeters of permeant vapor that will outgas from a square meter of the film material per day, under conditions where the material was initially saturated with the permeant.

The saturated condition can be readily obtained by merely exposing the material to the permeant for an extended time period, as for example, several days or weeks, or until an equilibrium condition is reached wherein no more permeant enters the material than escapes from the material through outgassing. The length of time required for this equilibrium condition to occur for any given film material can be determined through isostatic testing of the material under conditions known in the prior art.

The horizontal axis of the graph of FIG. 3 is calibrated in units of time, typically minutes or hours. The scale may be selected for any given material so as to show the outgassing curve for any time period of interest. FIG. 3 shows, therefore, a normalized outgassing curve for a typical material sample, and the curve is useful for comparing different samples of the same material, to detect an quantify differences in outgassing characteristics of the two material samples. Ultimately, this comparison will quantify the differences in transmission rate characteristics of the two material samples. In evaluating this material for its suitability as a gas or vapor barrier material for the permeant in question, one can conclude that the material will limit the permeant transmitted through it to a predetermined rate. The decision as to whether the material is satisfactory or unsatisfactory for use as a packaging material can now be made by experts who have knowledge of the maximum (or minimum) permeant transmission that can be tolerated for the package contents. For example, it might well be decided that this film material is unsatisfactory for packaging certain food types, because of flavor degradation or spoilage which will occur as air enters the package over time. A curve of the type shown in FIG. 3 can be developed for any film barrier material, using procedures which are well known in the prior art, under isostatic testing conditions. Unfortunately, the length of time required for such isostatic testing is considerable for any given sample, and therefore such tests are done infrequently, on a random or periodic sampling basis, to try to evaluate the quality of film being used for packaging.

The present invention enables a comparison of the permeant transmission characteristics of plastic or other barrier films on a real time basis, or at time intervals very much shorter than previously possible. To perform the inventive method, it is necessary to obtain an initial isostatic measurement of the film permeant transmission characteristic, to serve as a baseline comparison for subsequent online measurements. Thereafter, it is only necessary to obtain occasional partial outgassing data points, in order to make a viable comparison with the initial baseline data, and to make a viable comparison of the current film sample to the baseline film sample. The process works because it has been learned, through experimentation and calculation, that the exponential outgassing curve for a given material is the same, during the first several minutes of outgassing the film, whether the material is initially wholly saturated with a permeant, or whether the material is only partially saturated with a permeant. Furthermore, data points captured at the same relative outgassing time for two different samples of material can provide an accurate ratio of the two different transmission characteristics. which can be extrapolated to an actual measure of the transmission characteristic of either material if the other is known.

The process of determining the gas transmission rate of a film on an online basis requires a four-step measurement:

1) Obtain an isostatic measurement of the permeant transmission rate of the film, taken under isostatic conditions, to obtain the transmission rate (Tr) of a representative sample of the film; and 2) Obtain an online measurement of a data point (t1d) for the outgassing curve of the identical film, taken during the first several minutes of outgassing and using the apparatus described herein; and 3) Obtain an online measurement of a data point (t2d) for the outgassing curve of a different sample of the film, taken at the same relative time of outgassing; and 4) Multiply the transmission rate (Tr) determined according to step 1) by the ratio (t2d/t1d) to obtain the transmission rate of the different sample of the film.

A similar process may be employed using the apparatus of this invention by collecting data on a continuous basis, according to the following steps:

1) Same as step 1) above;

2) Obtain an online measurement of the accumulated permeant, accumulated over a predetermined time, for the identical film, using the apparatus described herein;

3) Obtain an online measurement of the accumulated permeant, accumulated over the same predetermined time, for a different sample of the film, using the apparatus described herein; and 4) Same as step 4) above.

Using the apparatus of FIG. 1A, it is possible to obtain the necessary measurements described above, and it is therefore possible to obtain an online measurement of the permeant transmission rate characteristic of a film sample as a step in the manufacturing process of the sample. The permeant to be measured, usually in gas or vapor form, is introduced into the material through chambers 10 and 20, and the outgassing of these same vapors or gases is measured as the material passes through chambers 50 and 60. Since any given section of the material will be present in chambers 10 and 20 for only a short period of time, the material will become only partially saturated with the gas or vapor. Likewise, since the material will be present in chambers 50 and 60 for only a short period of time, the gas or vapor absorbed into the film will only partially outgas during this time. However, if the respective chambers are made of sufficient length, relative to the linear speed of the material along the path of travel, it is possible to obtain a measurable quantity of vapor or gas for this purpose, as exemplified with reference to the following figures.

It should be noted that each of the following figures is intended to represent the outgassing curve only during the first brief time period of outgassing, as might be determined from data points collected from film material on a moving assembly line which progresses through the apparatus shown in FIG. 1A. In such case, if a particular film segment "df" were monitored as it passes through the apparatus, it will begin absorbing the vapor or gas as soon as it enters permeant chambers 20 and 30, and will continue absorbing the vapor or gas for so long as it travels through permeant chambers 20 and 30.

As the film segment "df" leaves chambers 20 and 30 it immediately begins outgassing the gas or vapor which it absorbed while it passed through chambers 20 and 30. If measurement chambers 50 and 60 are positioned in close downstream proximity to chambers 20 and 30, the outgassing vapor or gas will be collected in chambers 50 and 60 and conveyed to a suitable vapor or gas detector, where the measured vapor or gas content will be recorded as a data point.

The time base for collecting the data points can be continuous, or based on a relative value, determined by the linear travel speed of the film through the apparatus, so long as the same relative value is used for all measurements. For example, if the linear speed of travel of the film along the assembly line is 100 inches per minute, and the vapor or gas detector records a data point measurement every two minutes, the data point will be representative of the average transmission rate of each 200-inch segment of the film.

If the assembly line manufacturing tolerances gradually begin shifting toward an intolerable design condition, the data points collected over this period of time will also begin shifting, and eventually a data point will be recorded which indicates that the film design criteria has become out-of-specification, and corrective action can be taken to return the manufacturing process to nominal design characteristics.

Figure 4:
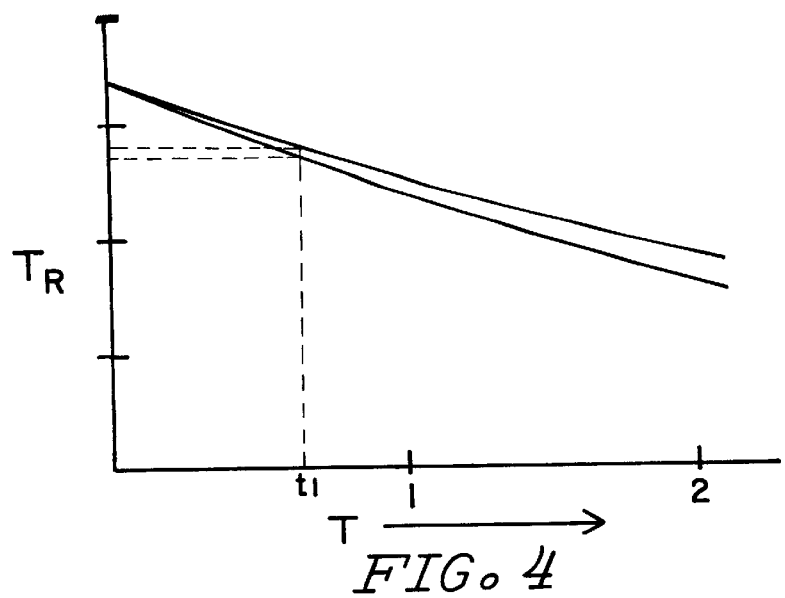
FIG. 4 is a graph showing transmission rate as a function of a very short time of two identical film materials, differing only in that one film is thicker than the other film.

FIG. 4 shows two outgassing curves for different samples of a film material, where the samples are of the same physical material, but of different thicknesses. If the outgassing data points are obtained at time=$t_1$, the transmission rate characteristics will show only a negligible variance as shown in FIG. 4.

Figure 5:
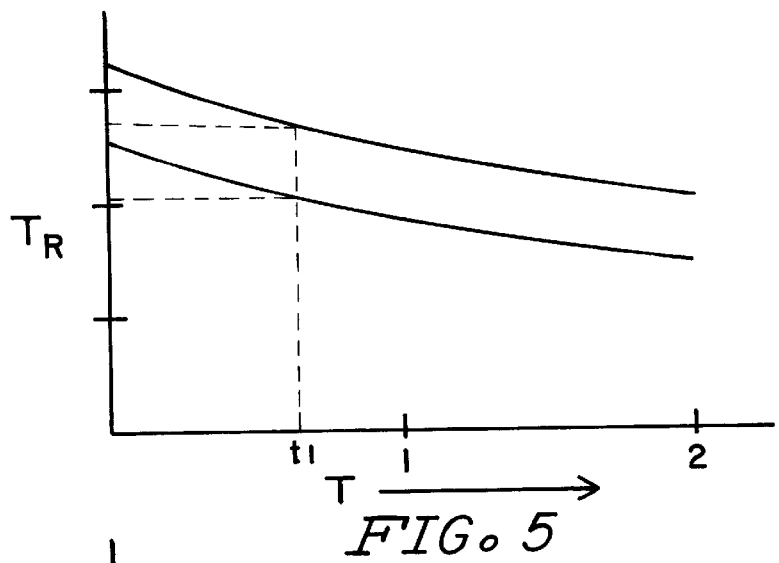
FIG. 5 is a graph similar to FIG. 4, showing transmission rates of two films of the same thickness, but wherein the film materials are differing in composition.

FIG. 5 shows two outgassing curves for different samples of film materials made from different compositions.

In this case, an outgassing data point obtained at time=$t_1$, shows a considerable variance between the two material samples.

Figure 6:
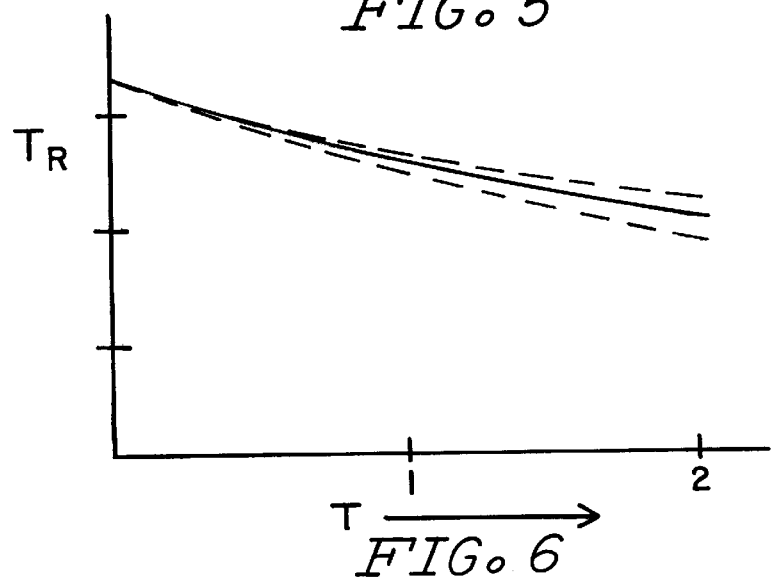
FIG. 6 is a graph similar to FIG. 4 and FIG. 5, showing the transmission rate as a function of time of a single material, with a permissible range of transmission rate deviation shown.

FIG. 6 shows a nominal outgassing curve in solid line, with an upper and lower dotted line variance, representing the range of permissible variation which can be tolerated for the material shown, given the design requirements for the film. If the measured outgassing data point falls outside the permissible range, the material is considered unacceptable as a packaging material for the product in question. In such case, the assembly line will probably be stopped until the manufacturing process parameters can be readjusted to bring the manufacturing tolerances back into specification.

The present invention may be embodied in other specific forms without departing from the spirit or essential attributes thereof; and it is, therefore, desired that the present embodiment be considered in all respects as illustrative and not restrictive, reference being made to the appended claims rather than to the foregoing description to indicate the scope of the invention.

What is claimed is:

1. An apparatus for monitoring the transmission rate characteristics of a permeant through a film material passing along a linear path of travel in sheet form at a relatively constant and predetermined rate of travel, comprising:

a) a first chamber enclosing a predetermined length of said path of travel, said first chamber having an inlet opening to receive film sheet material passing along said path of travel at a linear rate of travel, and having an outlet opening to permit the exit of film sheet material from said first chamber;

b) means for conveying a permeant into said first chamber;

c) a second chamber downstream of said first chamber, said second chamber having an inlet opening to receive film sheet material passing along said path of travel, and having an outlet opening to permit the exit of film sheet material from said second chamber;

d) means for conveying permeant outgassed from said film sheet material, while said film sheet material passes through said second chamber, to an exit conduit in said second chamber;

e) a permeant detector connected to said exit conduit, for detecting an amount of permeant outgassed in said second chamber, and for producing a signal responsive to said detected amount; and f) means for quantifying said signal and providing an indicator of the permeant transmission characteristics of said film sheet material.

2. The apparatus of claim 1, wherein said means for quantifying further comprises a computer processor having stored therein data representing the permeant outgassing characteristics of said material, and means for comparing the amount of permeant outgassing detected with the permeant outgassing characteristics stored for that material.

3. The apparatus of claim 2, wherein said means for conveying permeant outgassed from said film sheet material further comprises a source of inert gas and passages conveying a stream of said inert gas into said second chamber.

4. The apparatus of claim 3, further comprising timing means for operating said means for conveying permeant outgassed from said film sheet material; said timing means permitting actuation of said means for conveying for a time period at predetermined intervals.

5. The apparatus of claim 3, wherein said inert gas further comprises nitrogen.

6. The apparatus of claim 5, wherein said permeant further comprises water vapor.

7. An apparatus for comparing permeant transmission rates through film material passing along a path of travel with permeant transmission rate values established for said film material through isostatic testing of samples of said film material, comprising:

a) a first chamber along said path of travel, arranged to permit said film material to pass therethrough at a linear rate of travel;

b) a second chamber along said path of travel downstream from said first chamber, arranged to permit said film material to pass therethrough;

c) means for conveying a permeant into said first chamber;

d) a permeant detector connected to said second chamber, having conduit means for passing vapors collected in said second chamber to said detector, said detector having an output terminal for developing a signal representative of the quantity of vapors detected by said detector; and e) an electronic processor connected to said output terminal, said processor having means for generating a record of the quantity of vapors detected by said detector.

8. The apparatus of claim 7, further comprising means for conveying a permeant into said first chamber.

9. The apparatus of claim 8, further comprising a source of inert gas and a conduit connecting said source of inert gas to said second chamber, and wherein a mixture of said permeant and said inert gas in said second chamber constitute the vapors detected by said detector.

10. The apparatus of claim 9, wherein said electronic processor further comprises a programmed digital computer.

11. The apparatus of claim 10, wherein said inert gas further comprises nitrogen.

12. The apparatus of claim 11, wherein said permeant further comprises water vapor.

13. A method for comparing a permeant transmission rate characteristics of two material film samples by measurement of the permeant outgassing characteristics of said two material film samples, comprising the steps of:

a) conducting an isostatic test of a first material film sample, using said permeant, to determine the isostatic permeant transmission rate of said first material film sample;

b) absorbing said permeant into said first material film sample for a predetermined length of time;

c) detecting the amount of permeant outgassed from said first material film at selected increments of time;

d) absorbing said permeant into a second material film sample for said predetermined length of time;

e) detecting the amount of permeant outgassed from said second material film sample at any increment of time corresponding to at least one of said selected increments of time;

f) taking the ratio of the detected amount of permeant from said first material film sample to the detected amount of permeant from said second material film sample, both detected amounts being at the same increment of time, and multiplying said ratio by the isostatic permeation transmission rate of said first material film sample, to obtain the permeation transmission rate of said second material film; and g) moving said first and second material film samples along a path of travel at a linear rate of travel while steps b) through e) are performed.

14. The method of claim 13, further comprising the step, after step d), of mixing the permeant outgassed from said material sample with an inert gas.

15. The method of claim 14, wherein said inert gas further comprises nitrogen.

* * * * *